(12) United States Patent
Stumber

(10) Patent No.: US 9,555,229 B2
(45) Date of Patent: Jan. 31, 2017

(54) METHOD FOR PRODUCING SILICON MICRONEEDLE ARRAYS WITH HOLES AND MICRONEEDLE ARRAY

(71) Applicant: Robert Bosch GmbH, Stuttgart (DE)

(72) Inventor: Michael Stumber, Korntal-Muenchingen (DE)

(73) Assignee: Robert Bosch GmbH, Stuttgart (DE)

( * ) Notice: Subject to any disclaimer, the term of this patent is extended or adjusted under 35 U.S.C. 154(b) by 885 days.

(21) Appl. No.: 13/706,523

(22) Filed: Dec. 6, 2012

(65) Prior Publication Data

US 2013/0165872 A1   Jun. 27, 2013

(30) Foreign Application Priority Data

Dec. 23, 2011 (DE) .................... 10 2011 089 752

(51) Int. Cl.
*A61M 5/00* (2006.01)
*A61M 37/00* (2006.01)

(52) U.S. Cl.
CPC .. *A61M 37/0015* (2013.01); *A61M 2037/0053* (2013.01)

(58) Field of Classification Search
CPC ............... A61M 2037/003; A61M 2037/0053; A61M 2037/0038; A61M 37/0015; A61M 2037/0046
USPC ........................................................ 604/173
See application file for complete search history.

(56) References Cited

U.S. PATENT DOCUMENTS

| 8,419,708 | B2 * | 4/2013 | Tokumoto | A61M 37/0015 604/21 |
|---|---|---|---|---|
| 2004/0164454 | A1 * | 8/2004 | Gartstein | A61M 37/0015 264/293 |
| 2005/0011858 | A1 | 1/2005 | Kuo et al. | |
| 2006/0172541 | A1 | 8/2006 | Lee | |
| 2008/0245764 | A1 * | 10/2008 | Pirk | A61M 37/0015 216/2 |
| 2009/0030365 | A1 | 1/2009 | Tokumoto et al. | |

FOREIGN PATENT DOCUMENTS

| CN | 1526454 | A | 9/2004 |
|---|---|---|---|
| CN | 100998901 | A | 7/2007 |
| CN | 101879336 | A | 11/2010 |
| CN | 101912663 | A | 12/2010 |
| CN | 102068252 | A | 5/2011 |
| EP | 1 418 977 | A2 | 5/2004 |
| JP | 2008-246492 | A | 10/2008 |
| JP | 2011-72695 | A | 4/2011 |

* cited by examiner

*Primary Examiner* — Deanna K Hall
(74) *Attorney, Agent, or Firm* — Maginot, Moore & Beck LLP

(57) ABSTRACT

A method for producing silicon microneedle arrays with drilled holes includes producing a silicon microneedle array. For each microneedle in a plurality of microneedles in the microneedle array, a laser is positioned relative to a microneedle and a drilled hole is drilled into the microneedle array by laser drilling. The drilled holes are drilled in microneedles, in flanks of the microneedles or alongside microneedles. A microneedle array includes a substrate composed of a micromechanical semiconductor material. The microneedle array has microneedles that project from the substrate and has drilled holes. The microneedles are composed of a porous micromechanical semiconductor material.

5 Claims, 4 Drawing Sheets

METHOD FOR PRODUCING SILICON MICRONEEDLE ARRAYS WITH HOLES AND MICRONEEDLE ARRAY

This application claims priority under 35 U.S.C. §119 to patent application no. DE 10 2011 089 752.6, filed on Dec. 23, 2011 in Germany, the disclosure of which is incorporated herein by reference in its entirety.

BACKGROUND

The present disclosure relates to a method for producing silicon microneedle arrays with holes and to a microneedle array.

Microneedle arrays with through-holes are used in the cosmetic field and the medical field. Numerous processes exist for producing microneedles composed of metal, polymer and silicon. The microneedles composed of silicon are produced by methods of microsystems engineering, inter alia by lithography or mask processes and etching methods or patterning processes. Methods for producing silicon microneedle arrays with through-holes are likewise already known, for example from US 2005 011 858 A1, US 2006 172 541 A1 or CN 1 526 454 A. All the methods mentioned above use the mask processes and patterning processes from semiconductor fabrication to produce the through-holes. The known processes which produce needles with through-holes for filling the needles from the rear side, involve a very high outlay.

Furthermore, JP 2011 072 695 A discloses a method for producing polymer microneedle arrays with through-holes. The microneedle array is produced by means of a heat imprint method. Through-holes are subsequently produced in the needles by means of a femtosecond laser, wherein the laser beam coming from the flat substrate side penetrates through the substrate and subsequently penetrates into the needles.

SUMMARY

The present disclosure provides a method for producing silicon microneedle arrays with through-holes according to the description below and a microneedle array according to the description below.

According to the disclosure, a laser is positioned relative to a needle of a microneedle array, and a drilled hole is subsequently drilled into the microneedle array by means of the laser.

In the case of a microneedle array having an arrangement of the microneedles in a grid known per se, advantageously after a single positioning of the laser relative to a selected needle at a defined position, the array is traced in a grid-shaped fashion in accordance with the known grid.

One preferred embodiment provides for drilling holes in the needles and creating a silicon hollow needle array with low outlay.

A microneedle array comprising a substrate composed of a micromechanical semiconductor material is provided according to the disclosure, wherein microneedles project from the substrate, and wherein the substrate has drilled holes. The microneedle array has microneedles composed of a porous micromechanical semiconductor material.

The substrate preferably has a porous substrate layer adjoining the microneedles.

Preferably, the microneedle array has a smooth rear side and, opposite the latter, a needle side having the microneedles, wherein the drilled holes proceed from the rear side and are embodied as blind holes which end in the porous substrate layer.

The detailed description below discloses preferred developments.

Alternative embodiments provide for drilling holes laterally with respect to the needles and creating U-shaped needles or needles having a liquid-guiding channel, or drilling holes alongside the needles in the substrate of the array.

The present disclosure provides a possibility for producing a fluidic linkage of needles on a front side of a silicon microneedle array to a rear side of the Si microneedle array with low outlay.

A silicon hollow needle array can be used to deposit active substances at a defined depth below the surface of the skin.

Microneedles embodied as hollow needles often have an insufficiently sharp needle tip. With a silicon needle array with holes laterally with respect to the needles, in particular at the flanks near the needle tip, a better piercing behavior can be achieved since the holes are less frequently closed off by stamped-out shreds of skin during piercing.

A silicon microneedle array with holes alongside the needles makes it possible to load the needles with an active substance that penetrates deeply into the skin, and makes it possible to feed a second active substance onto the surface of the skin from the rear side of the microneedle array.

A further advantage of the disclosure is the flexibility that, independently of previous processes, laser processing is possible before or after singulation from the wafer on individual needle arrays.

Furthermore, there is design freedom—individual or many through-holes can be implemented, depending on the requirements of the respective current application.

An example of a suitable laser is an Nd:YAG laser at a wavelength of 1064 nm having a pulse frequency of 4 kHz. However, a wavelength of 532 nm or, in the case of corresponding available lasers, other wavelengths and other pulse frequencies are also possible. The holes produced by means of laser drilling have a funnel-shaped or virtually tubular contour depending on the focus setting.

Silicon needle arrays can have needles composed of solid silicon. The front side, i.e. the needle side of such silicon needle arrays is fluidically contacted preferably by means of perforation from the array rear side.

Silicon needle arrays can have needles composed of porous silicon, e.g. composed of porous silicon produced by means of electrochemical HF etching. On the one hand, the front side of such silicon needle arrays can be fluidically contacted by means of perforation from the array rear side, such that the desired liquids or substances can pass both along the surface and through the porous material into the body.

On the other hand, the drilled holes introduced from the array rear side can be embodied as blind holes which end in the porous layer. This enables fluidic contacting from the array rear side via the porous silicon layer into the epidermis. In this case, it is alternatively also possible firstly to drill holes into a solid silicon wafer and subsequently to produce a porous layer and the needle structure.

BRIEF DESCRIPTION OF THE DRAWINGS

The present disclosure is explained in greater detail below on the basis of the exemplary embodiments indicated in the schematic figures of the drawings.

The accompanying drawings are intended to impart a further understanding of the embodiments of the disclosure. They illustrate embodiments and in association with the description serve to clarify principles and concepts of the disclosure. Other embodiments and many of the advantages mentioned are evident with regard to the drawings. The elements of the drawings are not necessarily shown in a manner true to scale with respect to one another.

In the figures of the drawings, identical, functionally identical and identically acting elements, features and components—unless stated otherwise—are respectively provided with the same reference signs.

DETAILED DESCRIPTION

Figure 1:
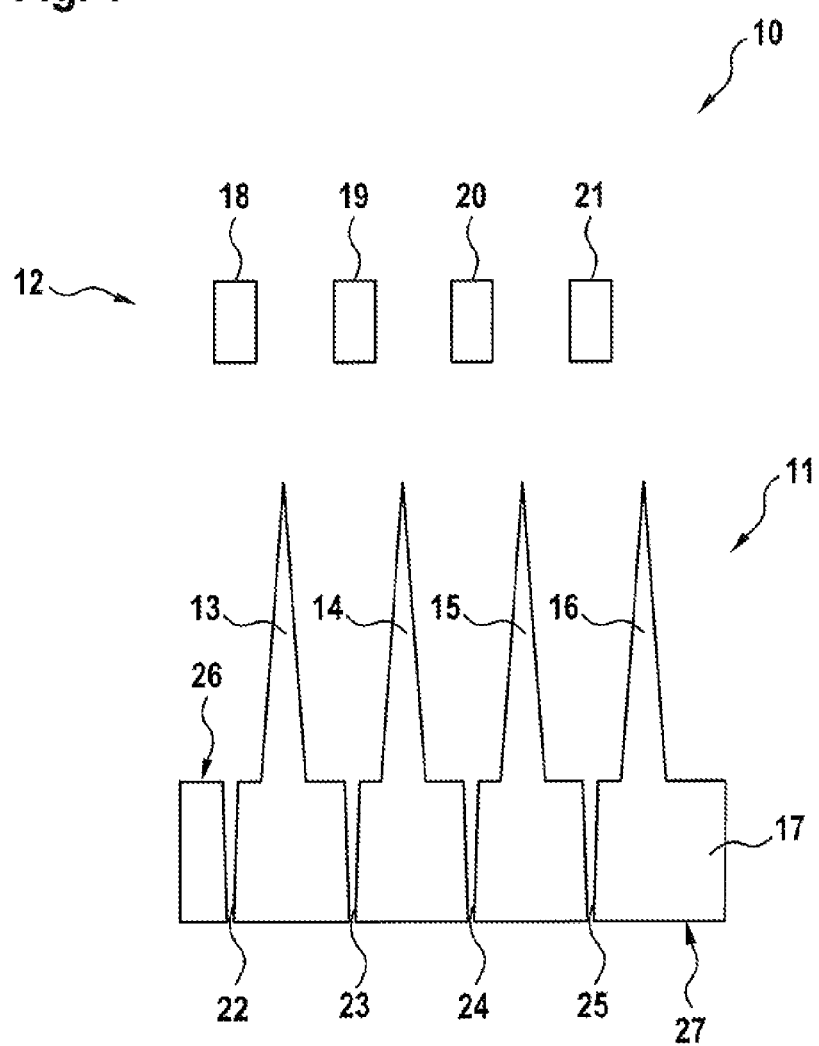
FIG. 1 shows a schematic illustration of a silicon needle array with through-holes drilled from the front side in the substrate and positions of a laser above the silicon needle array for carrying out the method in accordance with one embodiment.

FIG. 1 illustrates an arrangement 10 with a silicon needle array 11 and positions of laser optical units 12. The silicon needle array 11 has needles 13, 14, 15, 16 on a substrate 17. The laser positions 18, 19, 20, 21 are respectively assigned to the needles 13, 14, 15, 16. The laser positions 18, 19, 20, 21 are arranged here laterally alongside and above the needles 13, 14, 15, 16. With this arrangement 10 with the laser positions 18, 19, 20, 21 laterally alongside and above the needles 13, 14, 15, 16, drilled holes 22, 23, 24, 25 are drilled in the substrate 17 from a needle side, the front side 26 of the silicon needle array 11. In this case, the drilled holes 22, 23, 24, 25 in the substrate 17 are through-holes which fluidically connect the front side 26 of the silicon needle array 11 to the flat side, the rear side 27, thereof. The drilled holes 22, 23, 24, 25 are wider at the front side 26 than at the rear side 27 of the silicon needle array 11.

The laser positions 18, 19, 20, 21 of a laser are illustrated schematically as laser optical units 12 in FIG. 1. In practice, use is usually made of a laser having an individual laser optical unit that successively moves to the laser positions 18, 19, 20, 21 and drills the drilled holes 22, 23, 24, 25. In the case of a microneedle array such as silicon needle array 11 with an arrangement of the needles 13, 14, 15, 16 in a known grid, the laser is positioned once in laser position 18 relative to the selected needle 13, which lies at a defined position of the silicon needle array 11. Afterward, the laser moves to the further laser positions in accordance with the known grid and the grid is thus traced. By employing the same grid for the needles 13, 14, 15, 16 of the silicon needle array 11 and the laser positions 18, 19, 20, 21 the laser is positioned in all laser positions 18, 19, 20, 21 relative to corresponding needles 13, 14, 15, 16. With such an exact positioning of the laser, after single alignment it is possible to drill holes into the needles, into the flanks of the needles or, as shown in FIG. 1, alongside the needles into the substrate.

The silicon needle array 11 can consist of solid silicon or it can comprise a porous silicon. In particular, it is possible to load the at least 150 μm long needles 13, 14, 15, 16 at the tip with a first active substance and to bring a second active substance via the drilled holes 22, 23, 24, 25 to the front side 26 of the silicon needle array 11.

Figure 2:
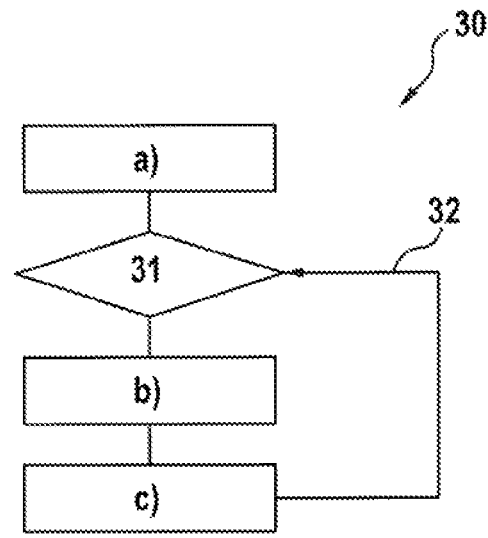
FIG. 2 shows a flowchart of the method for producing silicon microneedle arrays with holes in accordance with a further embodiment.

FIG. 2 shows a flowchart 30 of the method for producing silicon microneedle arrays with holes in accordance with a further embodiment of the present disclosure. The method starts with a first method step a) producing a silicon microneedle array having a flat side and a needle side. Proceeding from this silicon microneedle array, there then follow in a loop 31 two method steps for a plurality, in particular for all, all of the microneedles of the microneedle array. Initially, in a second method step b), a laser is positioned relative to a microneedle of the microneedle array. In this case, the laser can be positioned relative to the needle tip, relative to a position on the needle flank or relative to a position alongside the needle. Afterward, in a third method step c), a drilled hole is drilled into the microneedle array by means of laser drilling. After this method step, in accordance with arrow 32, the method proceeds to the start of the loop 31 and the loop is repeated until drilled holes have been drilled for all of the needles provided.

Figure 3:
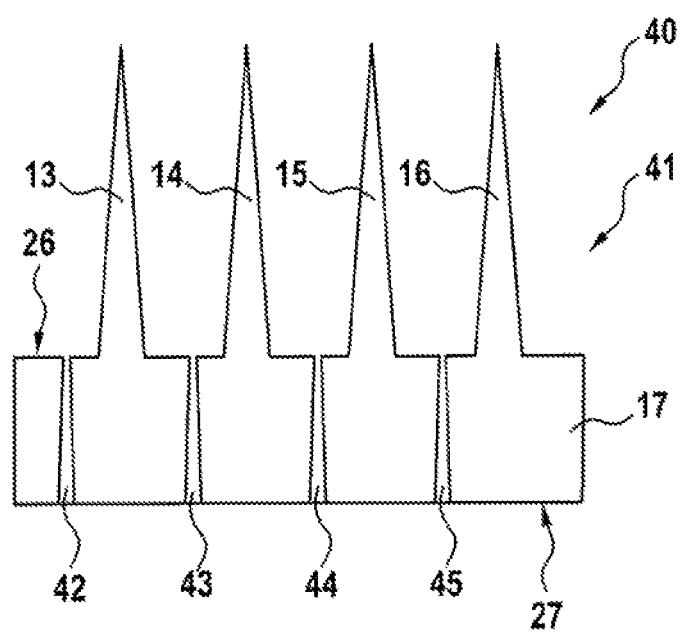
FIG. 3 schematically shows a silicon needle array with through-holes in the substrate of the array, which through-holes are drilled from the rear side in accordance with a further embodiment.

FIG. 3 schematically shows a silicon microneedle array 40 which, before the method according to the disclosure is carried out, corresponds to the silicon needle array 11 from FIG. 1 in the same stage, and corresponding thereto has needles 13, 14, 15, 16 projecting from a substrate 17. In accordance with one embodiment of the present disclosure, drilled holes 42, 43, 44, 45 are drilled as through-holes in the substrate 17 of the array from the rear side 27. The drilled holes 42, 43, 44, 45 therefore have a larger diameter at the rear side 27 than at the front side 26.

Figure 4:
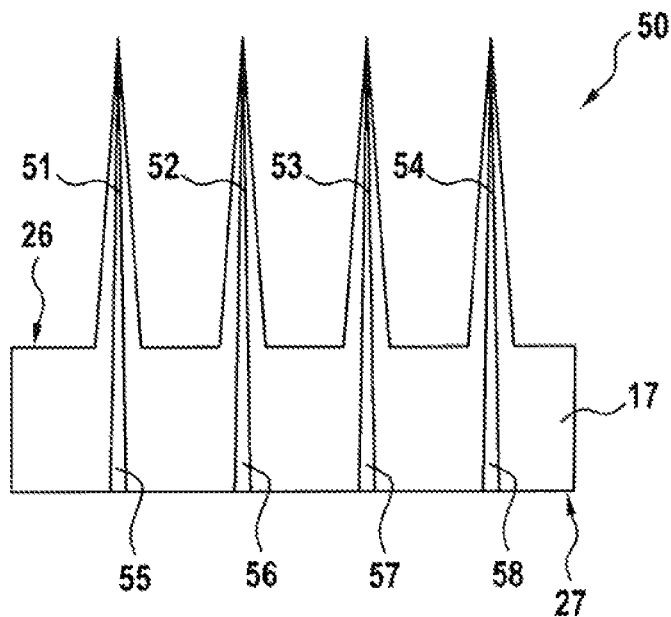
FIG. 4 schematically shows a silicon needle array with through-holes in needles of the array, which through-holes are drilled from the rear side in accordance with one embodiment.

FIG. 4 schematically shows a silicon needle array 50 which, before the method according to the disclosure is carried out, corresponds to the silicon needle array 11 from FIG. 1 in the same stage, and like the latter has needles 51, 52, 53, 54 projecting from a substrate 17. In accordance with one embodiment of the present disclosure, drilled holes 55, 56, 57, 58 are then drilled as through-holes in the needles 51, 52, 53, 54 of the array from the rear side 27. The drilled holes 42, 43, 44, 45 therefore have a larger diameter at the rear side 27 than at the needle tips on the front side 26 of the array.

Figure 5:
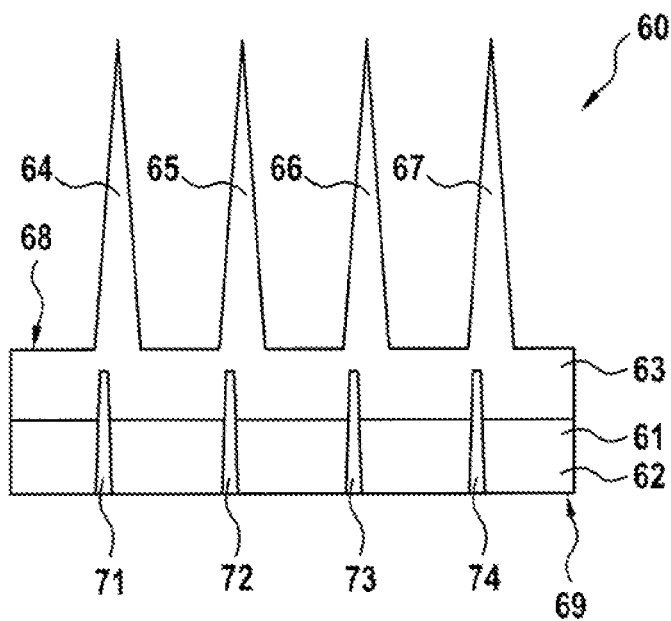
FIG. 5 schematically shows a silicon needle array with blind holes in the substrate of the array below the needles, which blind holes are drilled from the rear side in accordance with a further embodiment.

FIG. 5 schematically shows a silicon needle array 60 comprising a substrate 61, which has a silicon base substrate layer 62 composed of solid silicon and thereon a layer 63 composed of porous silicon, from which needles 64, 65, 66, 67 composed of porous silicon project. The layer 63 composed of porous silicon, which is adjoined by the needles, is conceptually assigned to the substrate, but the material progression between substrate and needles is homogeneous. The needles can be formed from an original substrate layer by a semiconductor fabrication process, for example, the thickness of which substrate layer corresponded to the thickness of the layer 63 plus the length of the needles 64, 65, 66, 67. The silicon needle array 60 again has a needle side, the front side 68, and a flat side, the rear side 69. In accordance with one embodiment of the present disclosure, drilled holes 71, 72, 73, 74 are then drilled as blind holes from the rear side 69 of the array below the needles 64, 65, 66, 67. The drilled holes 71, 72, 73, 74 penetrate through the silicon base substrate layer 62 composed of solid silicon and end in the layer 63 composed of porous silicon.

Figure 6:
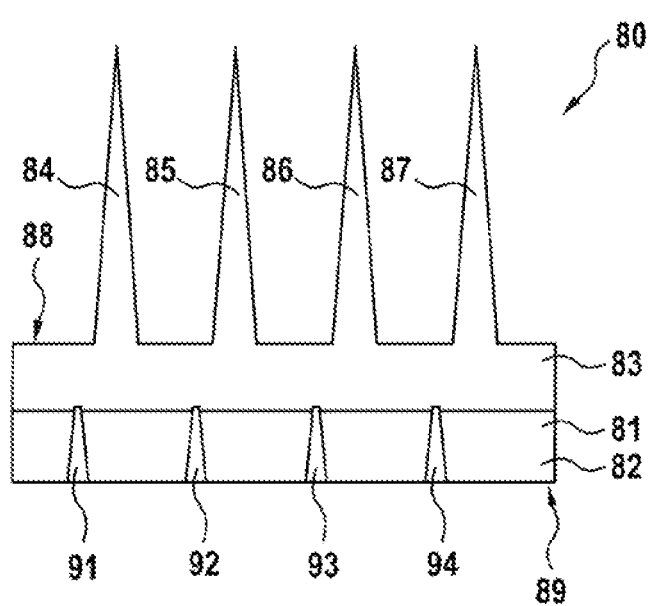
FIG. 6 schematically shows a silicon needle array with blind holes in the substrate of the array alongside the needles, which blind holes are drilled from the rear side in accordance with a further embodiment.

FIG. 6 schematically shows a silicon needle array 80 which is similar to the silicon needle array 60 from FIG. 5, but in contrast thereto now has the drilled holes—likewise embodied as blind holes—alongside the needles in the substrate. From the silicon needle array 80, the needles 84, 85, 86, 87 project from a substrate 81 having a silicon base substrate layer 82 composed of solid silicon and thereon a layer 83 composed of porous silicon. The silicon needle array 80 again has a needle side, the front side 88, and a flat side, the rear side 89. In accordance with this embodiment of the present disclosure, drilled holes 91, 92, 93, 94 are then drilled as blind holes from the rear side 89 of the array laterally alongside the needles 84, 85, 86, 87. The drilled holes 91, 92, 93, 94 penetrate through the silicon base substrate layer 82 composed of solid silicon and end in the layer 83 composed of porous silicon. Each of the needles 84, 85, 86, 87 has an assigned drilled hole 91, 92, 93, 94.

In order to highlight the utilization of the particular properties of porous silicon in the present disclosure, FIG. 6 shows drilled holes 91, 92, 93, 94 which penetrate only slightly into the layer 83 composed of porous silicon, compared with the thickness of the layer 83.

In the silicon needle array 60 from FIG. 5 and the silicon needle array 80 from FIG. 6, it is not necessary for a blind hole to be arranged alongside each needle in order to load each needle with active substance. Instead, in accordance with an embodiment not shown in a separate figure, it is possible for only a portion of the needles to have assigned drilled holes. On account of the porous structure of the needles, the active substance is distributed in the porous layer, namely the layer 63 and respectively 83 composed of porous silicon including the needles 64, 65, 66, 67 and needles 84, 85, 86, 87, respectively.

A further advantageously utilizable property of the needles composed of porous silicon is that the needles can release the active substance in a delayed fashion and that the needles deliver the active substance to the skin in a manner distributed over the needle surface.

A further embodiment (not shown) of the disclosure provides for a plurality of holes to be drilled into the same needle.

Electron microscope micrographs of silicon needle arrays according to the disclosure that have been drilled using an Nd:YAG laser having a pulse frequency of 4 kHz show, firstly, a very good positionability of the laser and thus of the drilled holes relative to needles of an array that are arranged in a grid-shaped fashion. Secondly, they make it possible to measure the drilled holes at the front and/or rear side. The funnel-shaped drilled holes examined as an example have entrance openings having a diameter of 50 μm to 70 μm and exit openings having a diameter of 10 μm to 20 μm. This applies both to through-holes drilled from the flat side of the microneedle array and to through-holes drilled from the needle side of the microneedle array. Typical needles have a length of 150 μm-250 μm and at the base a diameter of 30 μm-80 μm.

Although the present disclosure has been described fully above on the basis of preferred exemplary embodiments, it is not restricted thereto, but rather can be modified in diverse ways.

What is claimed is:

1. A microneedle array comprising:
   a substrate composed of a micromechanical semiconductor material and having drilled holes; and
   microneedles composed of the micromechanical semiconductor material and projecting from the substrate, wherein:
   the microneedle array has a planar rear side and a needle side opposite the rear side; and the microneedles are on the needle side,
   wherein the substrate has a porous layer adjoining the microneedles at the needle side, and
   wherein the drilled holes are blind holes that proceed from the rear side and end in the porous substrate layer before the needle side.

2. The microneedle array according to claim 1, wherein the blind holes are arranged below the microneedles.

3. The microneedle array according to claim 1, wherein the substrate has a relatively non-porous layer between the rear side and the porous layer.

4. The microneedle array according to claim 1, wherein the microneedles are porous.

5. The microneedle array according to claim 1, wherein the blind holes are arranged offset from the microneedles.

* * * * *